United States Patent
Nawrocki et al.

(10) Patent No.: US 8,226,684 B2
(45) Date of Patent: Jul. 24, 2012

(54) SURGICAL SUTURES HAVING COLLAPSIBLE TISSUE ANCHORING PROTRUSIONS AND METHODS THEREFOR

(75) Inventors: Jesse G. Nawrocki, Annandale, NJ (US); David C. Lindh, Sr., Flemington, NJ (US); Robert A. Rousseau, Ottsville, PA (US)

(73) Assignee: Ethicon, Inc., Somerville, NJ (US)

( * ) Notice: Subject to any disclaimer, the term of this patent is extended or adjusted under 35 U.S.C. 154(b) by 634 days.

(21) Appl. No.: 12/340,829

(22) Filed: Dec. 22, 2008

(65) Prior Publication Data

US 2010/0160961 A1    Jun. 24, 2010

(51) Int. Cl.
*A61B 17/04* (2006.01)
(52) U.S. Cl. ........................................ 606/228
(58) Field of Classification Search .................. 606/219, 606/228–232, 300, 304, 310; 623/23.64; 401/28
See application file for complete search history.

(56) References Cited

U.S. PATENT DOCUMENTS

| | | | |
|---|---|---|---|
| 3,123,077 A | 3/1964 | Alcamo | |
| 3,570,497 A | 3/1971 | Lemole | |
| 4,950,285 A | 8/1990 | Wilk | |
| 5,053,047 A | 10/1991 | Yoon | |
| 5,222,976 A | 6/1993 | Yoon | |
| 5,330,503 A | 7/1994 | Yoon | |
| 5,500,000 A | 3/1996 | Feagin et al. | |
| 6,506,190 B1 | 1/2003 | Walshe | |
| 6,712,859 B2* | 3/2004 | Rousseau et al. | 623/23.64 |
| 6,971,813 B2* | 12/2005 | Shekalim et al. | 401/208 |
| 7,021,316 B2* | 4/2006 | Leiboff | 606/222 |
| 7,588,594 B2* | 9/2009 | Sander et al. | 606/300 |
| 2006/0079935 A1 | 4/2006 | Kolster | |
| 2006/0276871 A1 | 12/2006 | Lamson et al. | |
| 2007/0005110 A1 | 1/2007 | Collier et al. | |

FOREIGN PATENT DOCUMENTS

| | | |
|---|---|---|
| DE | 4302895 | 8/1994 |
| FR | 2914178 A1 | 10/2008 |
| GB | 1506362 | 4/1978 |
| WO | WO 2005/055836 A2 | 6/2005 |
| WO | WO 2006/044494 A2 | 4/2006 |

* cited by examiner

Primary Examiner — Julian Woo

(57) ABSTRACT

A surgical suture includes a shaft having a leading end, a trailing end, and an outer surface extending between the leading and trailing ends. The surgical suture includes a plurality of flexible protrusions extending from the shaft, and a lumen extending between the leading and trailing ends of the shaft. The shaft includes a plurality of openings formed in the outer surface thereof that are in communication with the lumen. The shaft includes a first axial opening at the leading end thereof in communication with the lumen and a second axial opening at the trailing end thereof in communication with the lumen. A flowable material may be disposed in the lumen. After the surgical suture is implanted, the flowable material is adapted to pass from the lumen and through the plurality of openings in the outer surface of the shaft for contacting tissue surrounding the suture.

21 Claims, 9 Drawing Sheets

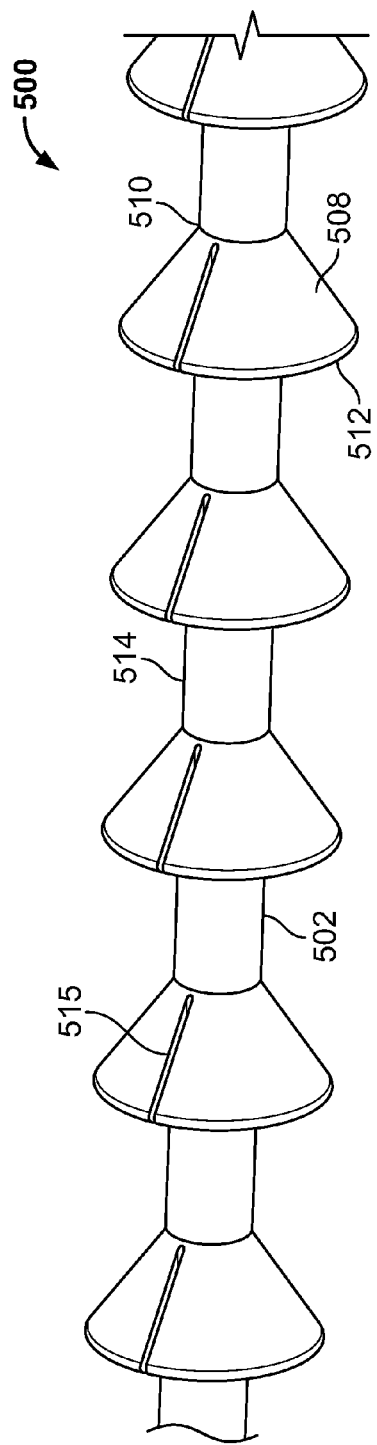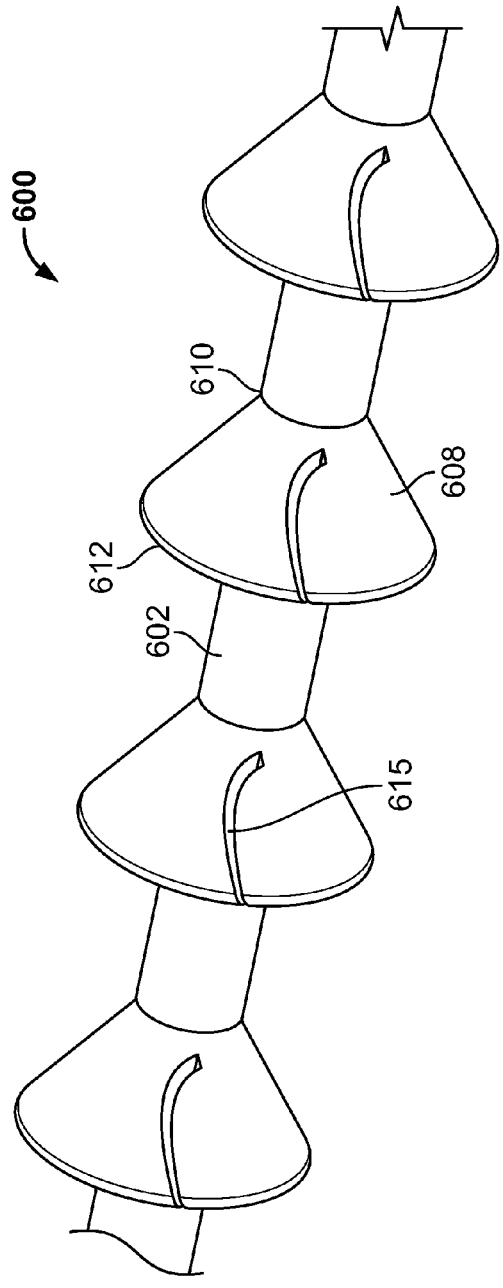
FIG. 8
FIG. 9

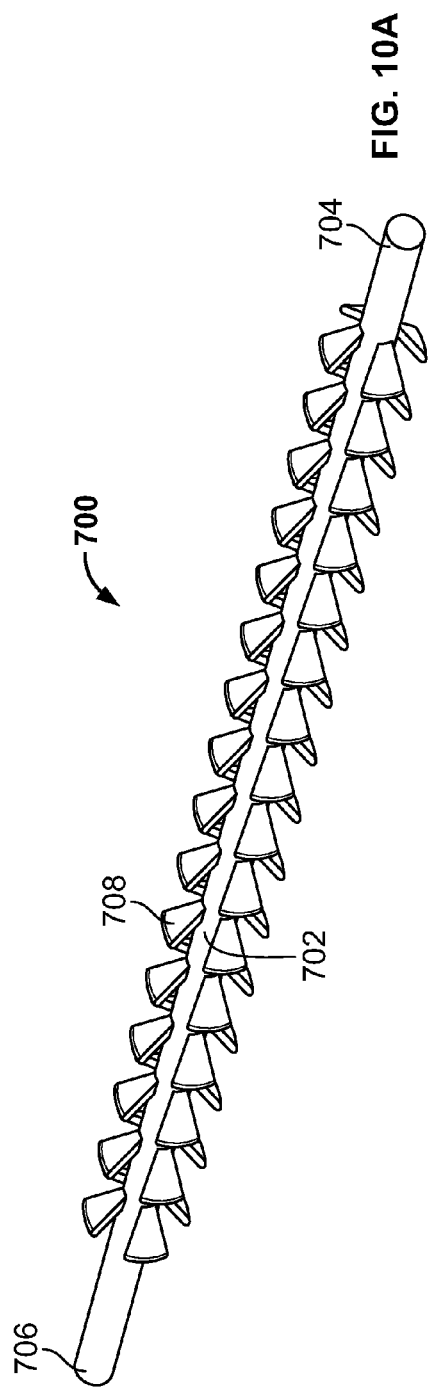
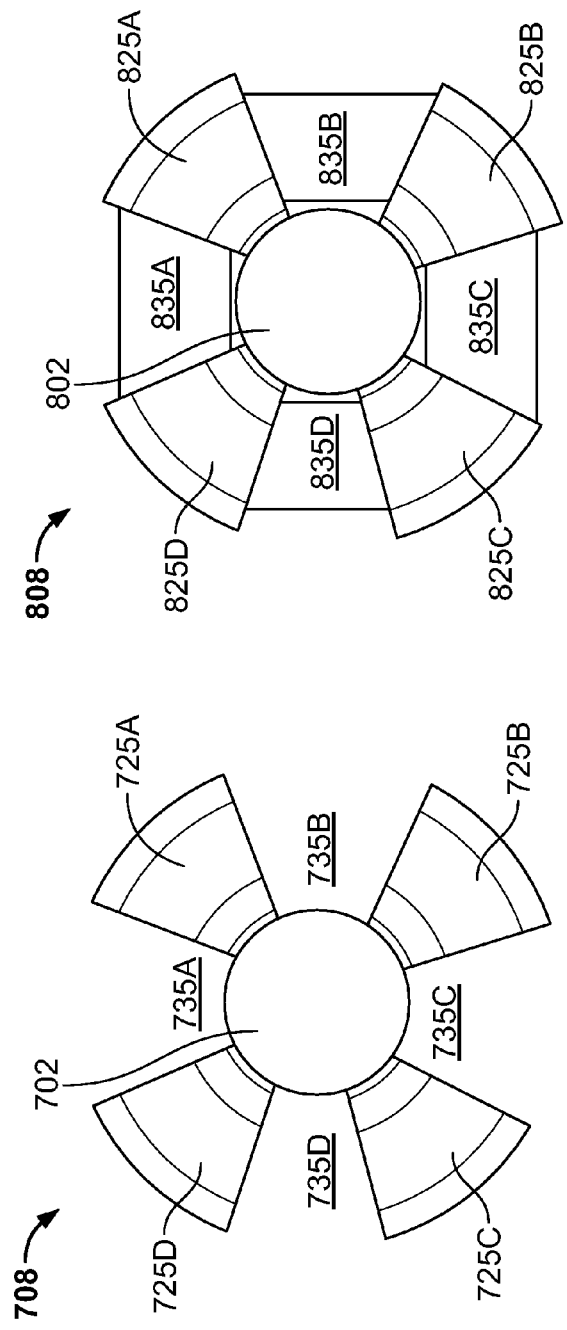
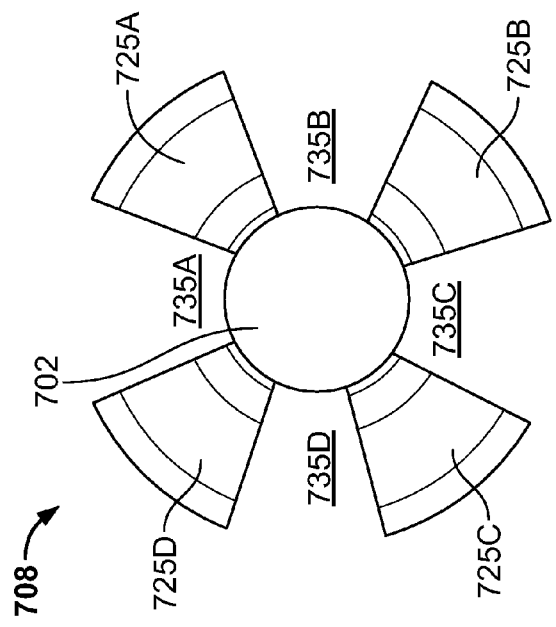

SURGICAL SUTURES HAVING COLLAPSIBLE TISSUE ANCHORING PROTRUSIONS AND METHODS THEREFOR

BACKGROUND OF THE INVENTION

1. Field of the Invention

The present invention generally relates to surgical sutures, and more specifically relates to surgical sutures having collapsible tissue anchoring protrusions for closing wounds and anchoring the surgical sutures in tissue and/or prosthetic devices.

2. Description of the Related Art

Surgical sutures are used for closing wounds and surgical incisions, and repairing damaged muscles, vessels, and tissue. Typically, a needle is attached to one end of the suture, and the needle is drawn through tissue to form one or more loops holding the tissue together. The suture is subsequently tied off in one or more knots so that the tissue will remain drawn together, or so that a prosthetic device will remain anchored in place.

Although conventional surgical sutures are very effective for closing wounds and incisions, there are a number of problems associated with these sutures. Many of these problems are directly related to the knots used to secure sutures in place. If the knots are not tied properly, defects may arise including slippage, knot breakage, and re-opening of the wound or incision. In addition, using knots to secure sutures may distort tissue, restrict blood flow, increase scar formation, impede wound healing, and result in infection.

In response to the deficiencies associated with conventional sutures, sutures having tissue engaging barbs have been developed. Unlike conventional sutures, barbed sutures have projecting barbs that allow the suture to be used to close wounds, approximate tissue, tighten tissue, and attach prosthetic devices without using knots. U.S. Pat. No. 5,931,885 discloses a barbed suture that is used for cosmetic procedures such as brow-lifts and face-lifts.

Referring to FIG. 1, a conventional barbed suture 20 may be formed by cutting a core thread 22 with a cutting blade 24. FIG. 1 illustrates an exemplary cut, whereby the cutting blade 24 first cuts into the core thread 22 at an angle β of approximately 30 degrees relative to a longitudinal axis x-x of the core thread to a depth of approximately 0.08 inches, and subsequently further cuts into the core thread for a distance of approximately 0.024 inches at an angle of approximately 0 degrees to form projecting barbs 26. After the cut is completed, each barb 26 remains connected to the core thread 22 through a base 28. During cutting, the core thread 22 is typically placed and held on a cutting vice or support in a manner well known in the art. A template may be used to guide the cutting blade 24.

Referring to FIG. 2, after the cutting steps described above, the cut barbs 24 remain flexibly coupled with the core thread 22 via the bases 28. When a leading end 30 of the barbed suture 20 is pulled in the direction $D_1$, the barbs 24 collapse inwardly toward the core thread 22, and deflect toward a trailing end 32 of the barbed suture 20. When the trailing end 32 of the barbed suture is pulled in the direction $D_2$, trailing edges 34 of the barbs 26 push against the surrounding media so as to deflect the barbs outwardly and away from the core thread 22. As the barbed suture is pulled in the direction $D_2$, great stress builds upon the previously cut base sections 28. As a result, one or more of the barbs 26 may fail at the base sections 28 and delaminate from the core thread 22. In applications where a significant or pulsatile load is placed on the barbed suture, i.e., heart valve repair or replacement procedures and orthopedic applications, a given barb may fail, or begin peeling away from the core thread. Once this occurs, due to the fibrous nature of the suture material, the barb may be stripped off the core thread along a significant length of the suture causing catastrophic failure of the suture, and may also result in serious injury to, or the death of, a patient.

In order to improve the reliability and durability of barbed sutures, there have been a number of attempts to enhance the strength of the connection between the barbs and the core thread. Unfortunately, these efforts have provided barbed sutures having rigid or relatively inflexible barbs provided along the barb shaft. The rigid barbs remain inflexible when pulled through tissue, impart significant drag, and damage tissue during passage. The drag and tissue damage effects become exaggerated when the barbed elements oppose each other along the barb shaft resulting in sawing of the tissue during motion.

In some instances, braided barbed sutures having more durable barbs are used. In one embodiment of commonly assigned U.S. Patent Application Publication No. 2007/0005110, the disclosure of which is hereby incorporated by reference herein, a prosthetic heart valve has a valve sewing ring and braided barbed sutures are disposed in the valve sewing ring by first passing the sutures through an annulus and then passing the sutures through the valve sewing ring. Approximately 12-20 sets of braided barbed sutures are passed through the valve sewing ring to secure the prosthetic heart valve in place. The heart valve is then parachuted down the sets of barbed sutures and seated in place within the annulus. After the heart valve has been parachuted down into place, the barbs prevent the valve from being moved in the opposite, upward direction for holding the heart valve in place without requiring knots.

In spite of the above advances, there remains a need for surgical sutures having improved reliability, durability and efficacy. In addition, there remains a need for surgical sutures that are easier to manufacture and deploy. There also remains a need for barbed sutures that cause little or no damage to tissue as the suture is passed through the tissue while retaining their structural integrity.

SUMMARY OF THE INVENTION

In one embodiment, a surgical suture includes a shaft having a length and an outer surface extending along the length of the shaft. The surgical suture desirably includes collapsible tissue anchoring protrusions extending from the outer surface of the shaft. In one embodiment, the flexible protrusions are similar to an umbrella whereby the device is passed through the tissue during installation and provide ease of insertion. After insertion, the flexible protrusions act to engage tissue and prevent device reversal from soft tissue through direct interference. This directional interference, coupled with the application geometry, serves to provide the means to approximate and secure wounds, or attach prosthetic devices to soft tissues without additional locking or securing features. When the surgical suture of the present invention is tensioned in the direction opposite of the direction of installation, the protrusions provide holding strength at multiple points around given sections of the shaft due to the abrupt vertical features located at the large ends of the protrusions coupled with a decreased ability of the protrusions to fold backwards. In one embodiment, the spacing between the adjacent flexible protrusions may be modified so that when the flexible protrusions collapse they bridge to the next set of protrusions so that the tissue is dilated and not continually dilating and constricting after each protrusion passes through.

In one embodiment, the surgical suture includes conical tissue-engaging elements that collapse symmetrically during insertion so as to decrease the force needed to pull the surgical suture through tissue or a prosthetic device. The collapsible tissue anchoring protrusions desirably collapse in a manner similar to an umbrella whereby they collapse easily during insertion, but provide significant holding strength when pulled in the opposite direction. In one embodiment, the collapsible tissue anchoring protrusions may be linked together by weaker sections such thinner sections or sections having perforations such as slits, living hinges, folds, or pleats so as to enable the anchoring member to collapse during insertion into the tissue.

Although the present invention is not limited by any particular theory of operation, it is believed that the surgical sutures disclosed herein may be pulled through tissue with minimal "sawing effect" and with no loss of core thread or fiber strength. In addition, the present invention provides a surgical suture having flexible protrusions that are configured to collapse inwardly toward the shaft in a uniform manner. The present invention also provides a surgical suture that includes a lumen for receiving a liquid material such as a pharmacological agent that is dispensed through radial openings in the suture after the suture is implanted. In addition, the present invention provides a composite surgical suture having varying flexibility, as well as a surgical suture having one or more absorbable sections and one or more non-absorbable sections.

In one embodiment, a surgical suture includes a shaft having a leading end, a trailing end, and an outer surface extending between the leading and trailing ends. The surgical suture includes a plurality of flexible protrusions extending from the shaft. The collapsible tissue anchoring protrusions may have various geometries including circular, conical, triangular, or any other well known geometry. The shaft desirably includes a lumen that is preferably disposed within the shaft and that is adapted to receive a flowable material. In one embodiment, the shaft includes a plurality of openings formed in the outer surface thereof that are in communication with the lumen. The lumen is desirably elongated and extends between the leading and trailing ends of the shaft. The shaft preferably includes a first axial opening at the leading end thereof that is in communication with the lumen and a second axial opening at the trailing end thereof that is also in communication with the lumen. A flowable material, such as a pharmacological agent, may be disposed within the lumen. After the suture is implanted in tissue, the flowable material is adapted to pass from the lumen and through the plurality of openings in the outer surface of the shaft for contacting the tissue.

In one embodiment, after the surgical suture is implanted, additional doses of the flowable material may be introduced into the lumen. For example, the flowable material may be provided within the lumen as the surgical suture is initially implanted in the tissue. Later, after all of the flowable material has passed through the openings in the outer wall of the shaft for contacting the tissue, one or more additional doses of the flowable material may be introduced into the lumen.

In one embodiment, at least one of the flexible protrusions on the outer surface of the shaft includes two or more flexible elements that are evenly spaced from one another around the outer surface of the shaft. The adjacent flexible elements are preferably spaced from one another by spaces or gaps extending between the opposing edges of the flexible elements. In one embodiment, at least one web extends between the opposing edges adjacent flexible elements. The web may include biocompatible materials, such as mesh, fabric, threads or tethers. In one embodiment, the shaft has a longitudinal axis extending between the leading and trailing ends thereof, and at least one of the webs extends in a direction that traverses the longitudinal axis. In one embodiment, at least one of the webs extends in a direction that is substantially perpendicular to the longitudinal axis of the shaft.

In one embodiment, a surgical suture includes a first axial opening provided at a leading end of the shaft and a second axial opening provided at a trailing end of the shaft. The first and second axial openings are in communication with the lumen extending through the shaft. The flowable material loaded within the lumen may include pharmacological agents, adhesive, epoxies, and polymers. The flowable material may be curable. In one embodiment, the flowable material may be introduced in a liquid state and then transformed into a partially cured state or a fully cured state. The partial or full curing desirably occurs after the flowable material has passed through the plurality of openings extending through the outer surface of the shaft.

In one embodiment, a surgical suture includes a shaft having a leading end, a trailing end, and an outer surface extending between the leading and trailing ends thereof. The surgical suture preferably includes a plurality of flexible protrusions or projections extending from the outer surface of the shaft, whereby at least one of the flexible protrusions includes two or more flexible elements evenly spaced from one another around the outer surface of the shaft. Spaces may be disposed or extend between adjacent edges of the adjacent flexible elements. At least one web desirably extends between the opposing edges of the adjacent flexible elements. In one particular embodiment, the flexible protrusion is divided into four flexible elements and four webs extend between the opposing edges of the flexible elements. In one embodiment, at least one web includes a mesh or a fabric that is biocompatible. In one embodiment, the shaft of the surgical suture desirably has a longitudinal axis extending between the leading and trailing ends thereof and at least one of the webs extends in a direction that traverses the longitudinal axis of the shaft.

In one embodiment, the shaft includes an elongated lumen extending between the leading and trailing ends thereof and a plurality of openings formed in the outer surface of the shaft that are in communication with the elongated lumen. The suture may include a first axial opening at the leading end of the shaft and a second axial opening at the trailing end of the shaft. The first and second axial openings are desirably in communication with the elongated lumen. The surgical suture also desirably includes a flowable material that is introducible into one of the first and second axial openings and into the elongated lumen. The flowable material may be introduced before the surgical suture is implanted into tissue. In one embodiment, the flowable material may also be introduced into the elongated lumen after implantation of the surgical suture. The flowable material is adapted to pass through the openings in the outer surface of the shaft after the surgical suture has been implanted in the tissue. The flowable material may be selected from a group of flowable materials including liquid pharmaceutical agents, phase changing liquids, curable fillers, curable adhesives and curable glues.

In one embodiment, a surgical suture includes a composite surgical suture having one or more tissue engaging elements, each including a shaft having flexible protrusions, and one or more filaments coupled and/or extending between the tissue engaging sections. The filaments may include a monofilament or a multi-filament structure. One portion of the surgical suture may be absorbable and another portion of the surgical suture may be non-absorbable or absorbable. In one particular embodiment, one or more of the tissue engaging elements may be non-absorbable and one or more of the filament sections of the composite surgical suture may be absorbable. In another embodiment, both the tissue engaging elements and the filament sections may be absorbable or non-absorbable.

In one embodiment, a surgical suture includes a shaft having collapsible tissue engaging protrusions extending therefrom. The shaft of the surgical suture is hollow and a filament, monofilament, or braided suture material may pass through the hollow center of the shaft. In another embodiment, the hollow center of the shaft may be used to deliver liquids such as pharmaceutical agents. In one embodiment, the shaft of the surgical suture may have a cross-section that is circular, triangular, square, or have another geometric shape. In one embodiment, the shaft of the surgical suture is an elongated tube.

In one embodiment, the flexible protrusions may be interconnected by sections having perforations, pleats, folds, partial slits that are either linear or curvilinear, or other structures that enable collapsing of the flexible protrusions. In one embodiment, each of the flexible protrusions may include a series of individual flexible elements that are separated from one another by one or more slits or spaces. The individual flexible elements may be tethered together by a filament or by a thin collapsible web. The individual flexible elements may also be tethered to the shaft by a filament or a thin collapsible web.

The collapsible tissue anchoring protrusions may have a variety of different shapes. In one embodiment, the collapsible tissue anchoring protrusions have a conical shape. In other embodiments, the shapes may be bell-like, oval, triangular, and square. Similarly, the shaft may have a cross-section having any of the above geometries or shapes.

The surgical suture desirably has a filament-like appearance. The surgical suture may be manufactured as a modular device and may be produced using a surgical needle attached to each end to aid in passing the device through tissue. The device may be produced from any materials such as polymers, metals, ceramics, composites, and preferably an absorbable or non-absorbable polymeric material. The specific choice of the material is desirable dependent upon the specific surgical application.

In one embodiment, the surgical suture includes a shaft having an elongated central lumen through which another device may pass. In one particular embodiment, a suture, monofilament or multifilament may pass through the lumen of the shaft. The suture may be fixed to the shaft via heat setting, ultrasonic welding, radio frequency, adhesive or any other bonding method well known to those skilled in the art. The filament portion of the suture may be made of the same or different material than the tissue holding portion of the surgical suture. In one embodiment, the sections of the suture having the collapsible tissue anchoring elements may be made of a material that is stronger and stiffer than the suture material that runs through the lumen so that the device may be more flexible in certain portions and less flexible in other portions.

In one embodiment, the lumen of the shaft may be used to deliver a liquid medium such as a pharmaceutical agent or an adhesive. The liquid medium may be delivered through the ends or openings along the length of the device. The lumen may also serve as a wound drain. In one embodiment, needles may be attached to one or both ends of the surgical suture to aid in passing the surgical suture through tissue or prosthetic devices.

In one embodiment, the collapsible tissue anchoring protrusions may be formed by making slits that allow the flexible tissue engaging elements to collapse onto the shaft. The slits may be formed starting from the outer portion of the anchoring element toward the shaft. In one embodiment, the slits do not extend completely to the shaft. In one embodiment, one or more of the tissue anchoring protrusions has a plurality of slits. The slits may be evenly spaced from one another around the perimeter of the shaft. The slits may include different geometries including straight lines and curves.

Although the present invention is not limited by any particular theory of operation, it is believed that providing flexible protrusions having weakened portions such as pleats allows the protrusions to more easily collapse inwardly toward the shaft. In one embodiment, the flexible protrusions include slits instead of pleats. The slits desirably allow the protrusions to collapse inwardly in a controlled fashion. Thus, the inward collapse of the protrusions is predictable and repeatable.

These and other preferred embodiments of the present invention will be described in more detail below.

BRIEF DESCRIPTION OF THE DRAWING

FIG. 8 shows a side view of a surgical suture having flexible protrusions, in accordance with one embodiment of the present invention.

FIG. 9 shows a side view of a surgical suture having flexible protrusions, in accordance with one embodiment of the present invention.

FIG. 10A shows a perspective view of a surgical suture having flexible protrusions, in accordance with one embodiment of the present invention.

FIG. 10B shows a cross-sectional view of the surgical suture of FIG. 10A taken along line 10B-10B of FIG. 10A, in accordance with one embodiment of the present invention.

FIG. 11 shows a cross-sectional view of a surgical suture having flexible protrusions divided into spaced flexible elements and webs extending between the spaced flexible sections, in accordance with one embodiment of the present invention.

DETAILED DESCRIPTION

Figure 1:
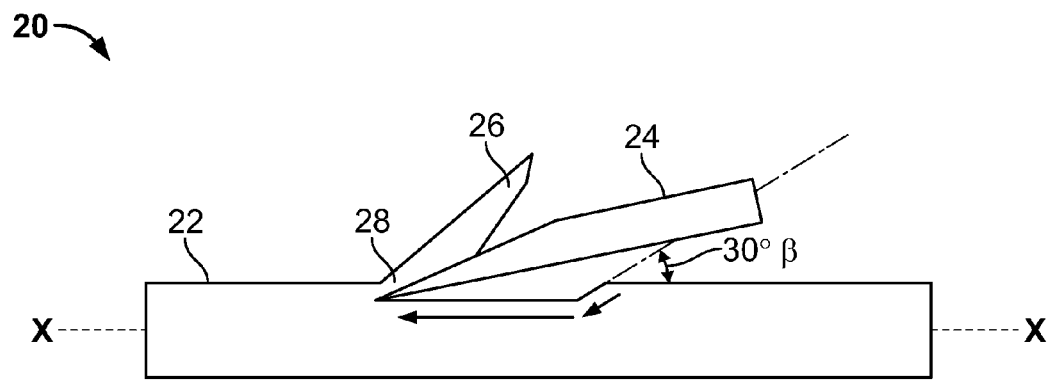
FIG. 1 shows a conventional method of making a barbed suture.
Figure 2:
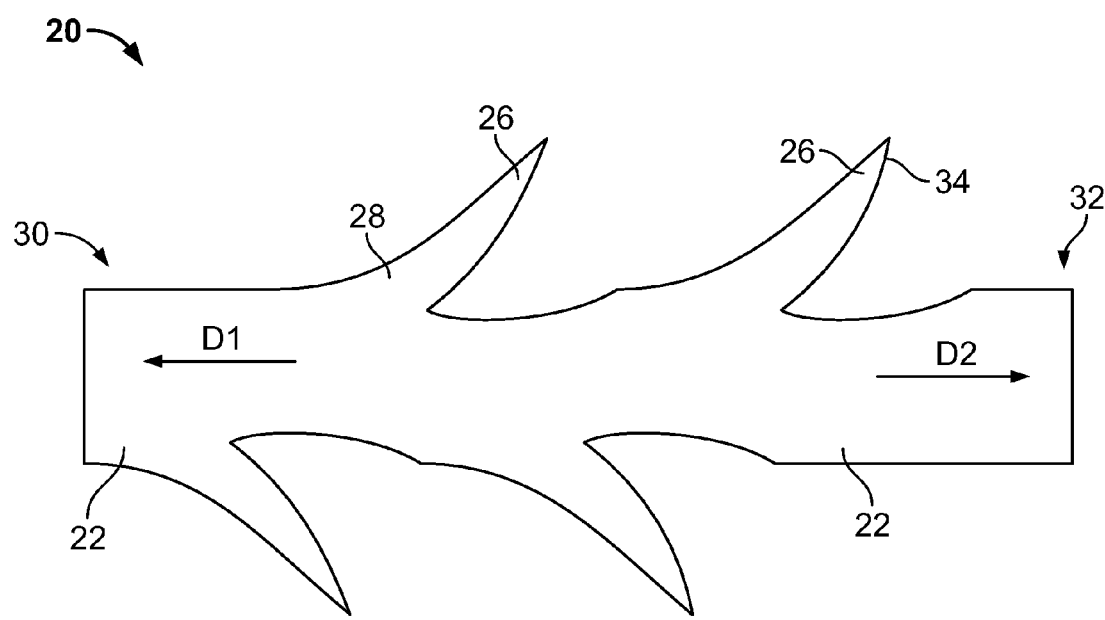
FIG. 2 shows a side view of a conventional barbed suture.
Figure 3A:
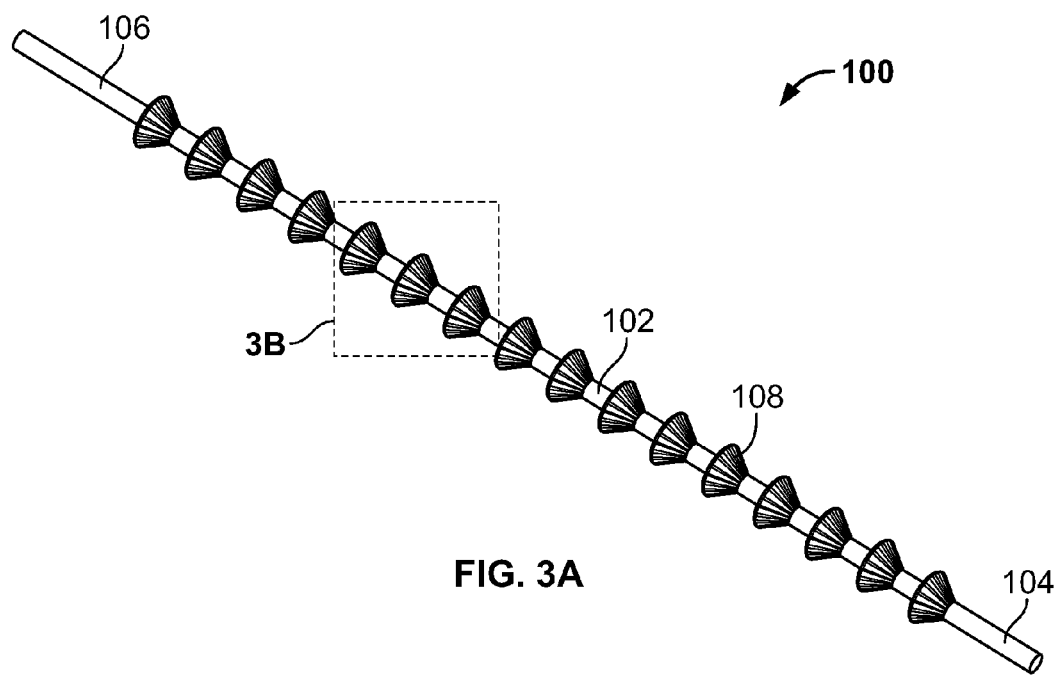
FIG. 3A shows a perspective view of a surgical suture having flexible protrusions, in accordance with one embodiment of the present invention.

Referring to FIG. 3A, in one embodiment, a surgical suture 100 includes an elongated shaft 102 having a leading end 104 and a trailing 106. The elongated shaft is desirably flexible so that the shaft may flex and bend as the surgical suture 100 passes through tissue and/or prosthetic components. The surgical suture desirably includes a plurality of flexible protrusions 108 that extend outwardly from the elongated shaft 102. The flexible protrusions are adapted to collapse inwardly toward the shaft as the leading end 104 of the suture is pulled through tissue or a prosthetic device.

Figure 3B:
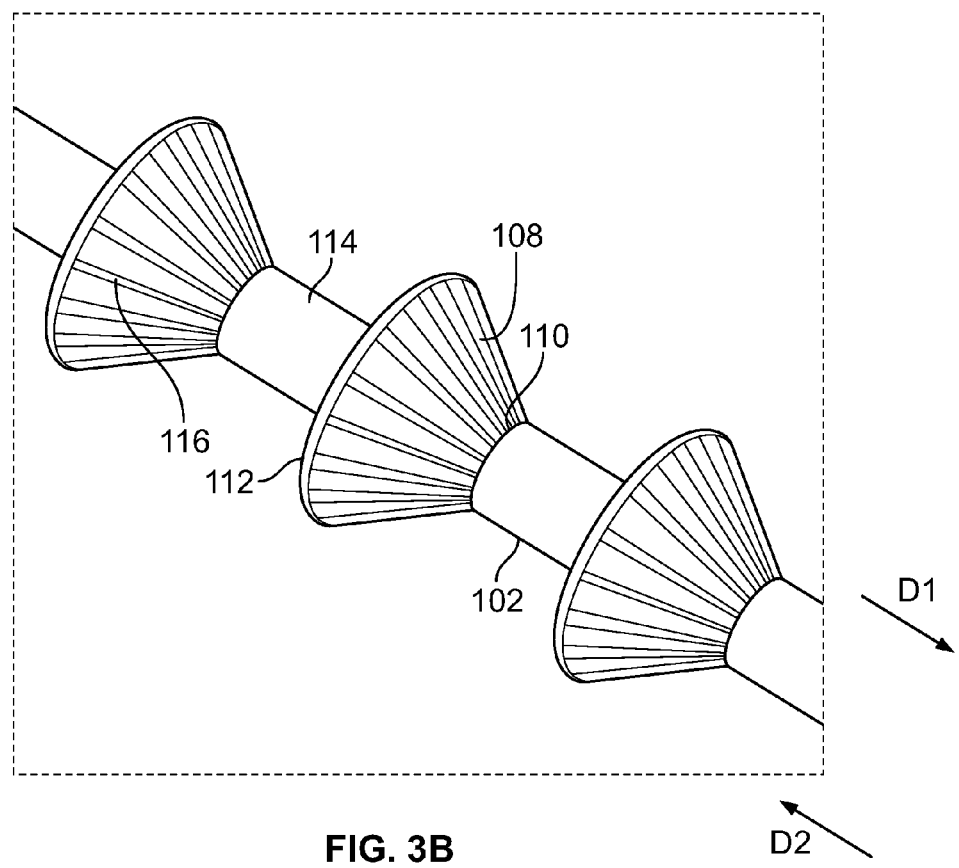
FIG. 3B shows an expanded view of a portion of the surgical suture shown in FIG. 3A.

Referring to FIG. 3B, in one embodiment, each of the flexible protrusions 108 includes a base 110 adjacent the shaft 102 and a flared ring 112 that is spaced from the outer surface 114 of the shaft 102. In one embodiment, the diameter of the flared ring 112 is larger than the diameter of the base section 110.

In one embodiment, each of the flexible protrusions 108 has one or more weakened areas 116 formed therein that facilitate flexing or collapsing of the protrusion at the weakened areas. In one embodiment, the weakened areas 116 are defined by a plurality of pleats that desirably extend between the base 110 and the flared ring 112 of each flexible protrusion 108. The weakened areas 116 (e.g. the pleats) provide control over how the flexible protrusion collapses inwardly toward the shaft. Although the present invention is not limited by any particular theory of operation, it is believed that providing the weakened areas in a particular pattern will provide more uniform control over how the flexible protrusions collapse inwardly so as to enhance the efficiency of the surgical suture when used for a particular type of operation. In one embodiment, a plurality of the flexible protrusions may have a similar pattern of weakened areas so that they all collapse inwardly in a particular manner.

Referring to FIG. 3B, in one embodiment, the flexible protrusions 108 are adapted to collapse in a manner similar to an umbrella when the surgical suture is passed in the direction $D_1$ through tissue during implantation. The flexible protrusions provide ease of insertion and minimize resistance as the surgical suture is pulled through the tissue. After implantation of the surgical suture, the protrusions 108 engage tissue so as to prevent device reversal in the direction $D_2$. If the surgical protrusions are pulled in the opposite direction $D_2$, the flexible protrusions 108 engage tissue so as to prevent device reversal through direct interference between the flared edge 112 of the flexible protrusions 108 and the soft tissue. Although the present invention is not limited by any particular theory of operation, it is believed that the directional interference, combined with the application geometry, serves to provide a surgical suture for securing wounds and/or attaching prosthetic devices to soft tissue without requiring additional locking or securing features. After implantation, if tension is applied to the surgical suture in the direction $D_2$, the flexible protrusions 108 provide holding strength at a plurality of locations along the length of the shaft 102 through the larger diameter flared edge sections 112 of the flexible protrusions 108. In one embodiment, the spacing between the adjacent flexible protrusions may be modified so that when the flexible protrusions collapse they bridge to the next set of protrusions so that the tissue is dilated and not continually dilating and constricting after each protrusion passes through.

Referring to FIG. 3A, in one embodiment, as the leading end 104 of the surgical suture 100 is pulled in the direction $D_1$, the flexible protrusions 108 collapse inwardly toward the shaft 102. The flexible protrusions 108 collapse in a manner similar to an umbrella whereby they collapse easily in the direction of insertion $D_1$, but provide significant holding strength in the opposite direction $D_2$. In one embodiment, the flexible protrusions 108 are linked together by weaker sections to enable the flexible protrusions to collapse easily during insertion into tissue. In preferred embodiments, the flexible protrusions include weakened sections that may be formed using slits, hinges, folds, or pleats. The weakened sections of the flexible protrusions may also be formed by thinning sections of the flexible protrusion.

The flexible protrusions 108 may have a variety of different shapes. In the particular embodiment shown in FIG. 3B, the surgical suture includes an elongated shaft 102 having a cylindrical shape with conical-shaped flexible protrusions 108 projecting from the shaft. In other embodiments, however, other shapes such as flexible protrusions having a bell-like form, an oval shape, a triangular shape and/or a square shape are possible. Moreover, in one or more embodiments, the shaft 102 may have a cross-sectional shape having any one or more of the above-mentioned geometries.

The surgical suture may include flexible protrusions provided over a portion or the entire length of the shaft 102. In one embodiment, the surgical suture may be a bi-directional surgical suture including a first set of flexible protrusions oriented in one direction for resisting movement of the shaft in a first direction and a second set of flexible protrusions oriented in an opposite direction for resisting movement of the shaft in a second, opposite direction.

Referring to FIG. 3A, in one embodiment, a surgical suture 100 may be provided as a modular device having a surgical needle attached to each of the leading and trailing ends 104, 106 to aid in passing the device through tissue. The surgical suture may be formed from a plurality of materials such as polymers, metals, ceramics, composites, and more preferably, an absorbable or non-absorbable polymeric material. The choice of materials may depend upon the specific surgical application.

Figure 4A:
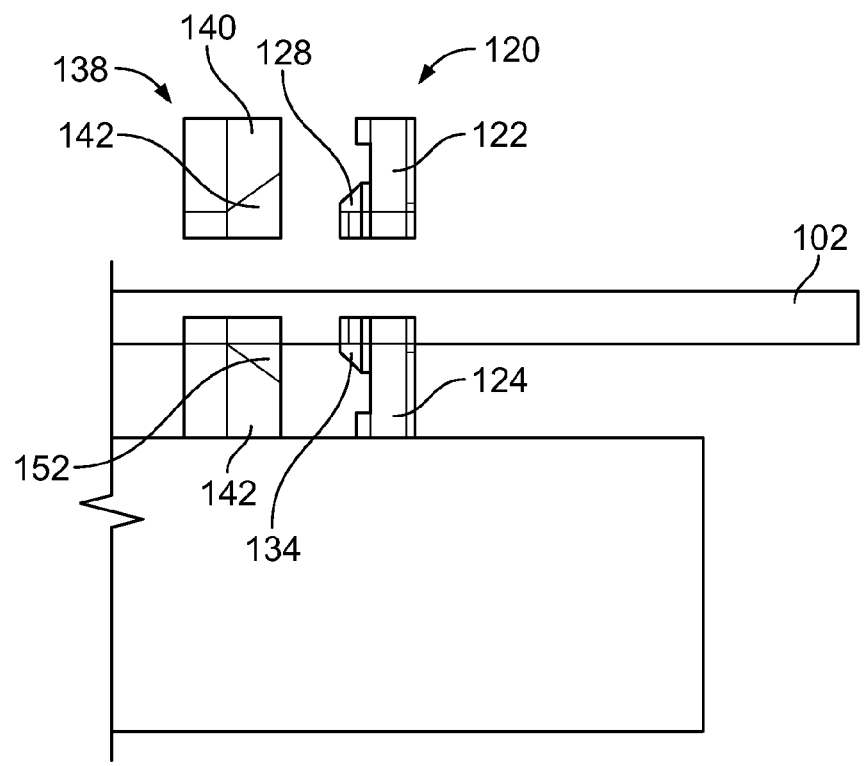
FIGS. 4A-4D show a method of making a surgical sutures having flexible protrusions in accordance with one embodiment of the present invention.

Referring to FIG. 4A, in one embodiment, a method of making surgical sutures having flexible protrusions includes providing a male die 120 having a first clamping part 122 and a second clamping part 124. The first clamping part 122 of the male die 120 includes an inner face having a first half of a conical-shaped protrusion 128 projecting therefrom. The first clamping part 122 of the male die also includes an outer face. The second clamping part 124 of the male die 120 includes an inner face having a second half of a conical-shaped protrusion 134 projecting therefrom.

The system also preferably includes a female die 138 having a first clamping part 140 and a second clamping part 142. The first clamping part 140 of the female die 138 includes an inner face defining a first half of a conical-shaped depression 142. The second clamping part 142 of the female die 138 includes an inner face defining a second half of a conical-shaped depression 152.

Referring to FIG. 4A, in one embodiment, during one stage of the process, the first and second clamping parts of the respective male and female dies 120, 138 are opened and an elongated shaft 102 is positioned between the first and second clamping parts.

Figure 4B:
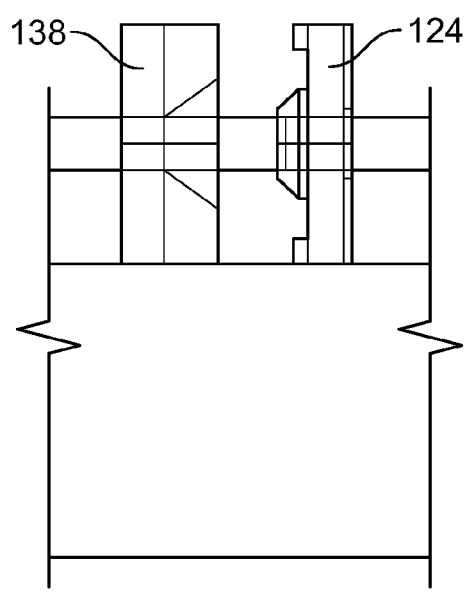

Referring to FIG. 4B, with the elongated shaft 102 positioned between the open clamping parts of the male die 124 and the female die 138, the opposing clamping parts are closed to engage the outer surface of the shaft 102. In one embodiment, the male and female dies 124,138 are heated to transfer heat to the shaft 102 so that the shaft is heated to a desired temperature for enabling the shaft to be molded by the male and female die.

Figure 4C:
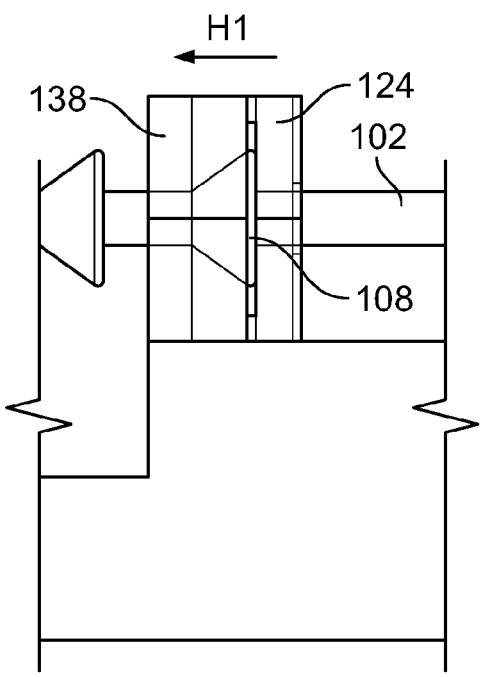

Referring to FIG. 4C, in one embodiment, after the male and female die 124, 138 heat the shaft 102 to a preferred molding temperature, the closed male die 124 is moved in the direction $H_1$ toward the closed female die 138 to shape a portion of the shaft 102 into a conical-shaped protrusion 108.

In one embodiment, as the male die 124 moves toward the female die 138, the overall length of the shaft 102 is shortened. In one preferred embodiment, the die tooling moves relative to the shaft 102 to compensate for the shortening of the shaft.

In one embodiment, the outer surfaces of the male and female dies that form the flexible protrusions 108 may include folds or perforations that are embossed into the protrusion during a protrusion forming stage. In one embodiment, as the closed male die 124 moves toward the closed female die 138 to form the protrusion, folds or perforations are embossed into the conical-shaped protrusion 108 using the male and female dies.

Figure 4D:
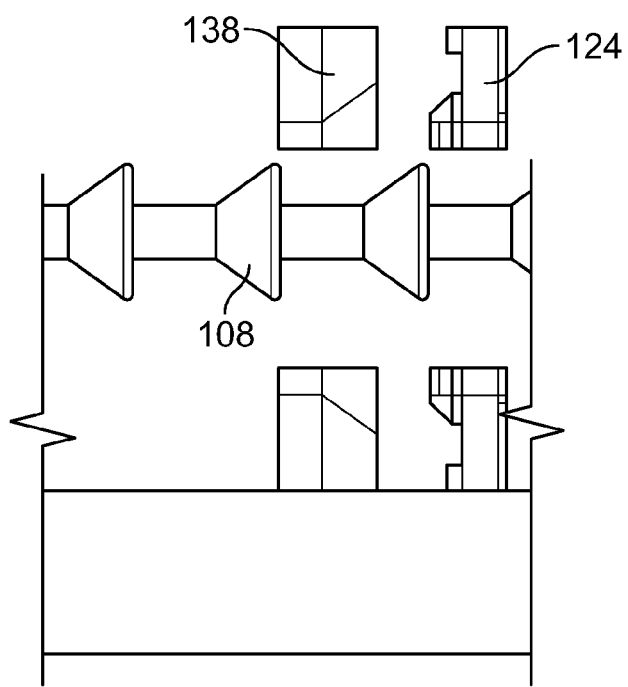

Referring to FIG. 4D, in one embodiment, after the protrusion 108 is formed, the protrusion is cooled while remaining in contact with the closed male and female dies 124, 138. In one embodiment, the protrusion cools after being removed from engagement with the male and female dies.

Referring to FIG. 4D, in one embodiment, the male and female dies 124, 138 are opened to expose the conical-shaped protrusions 108 to ambient air, preferably for cooling. The steps shown in FIGS. 4A-4D may be repeated to form a plurality of flexible protrusions along the length of the shaft 102.

Figure 5:
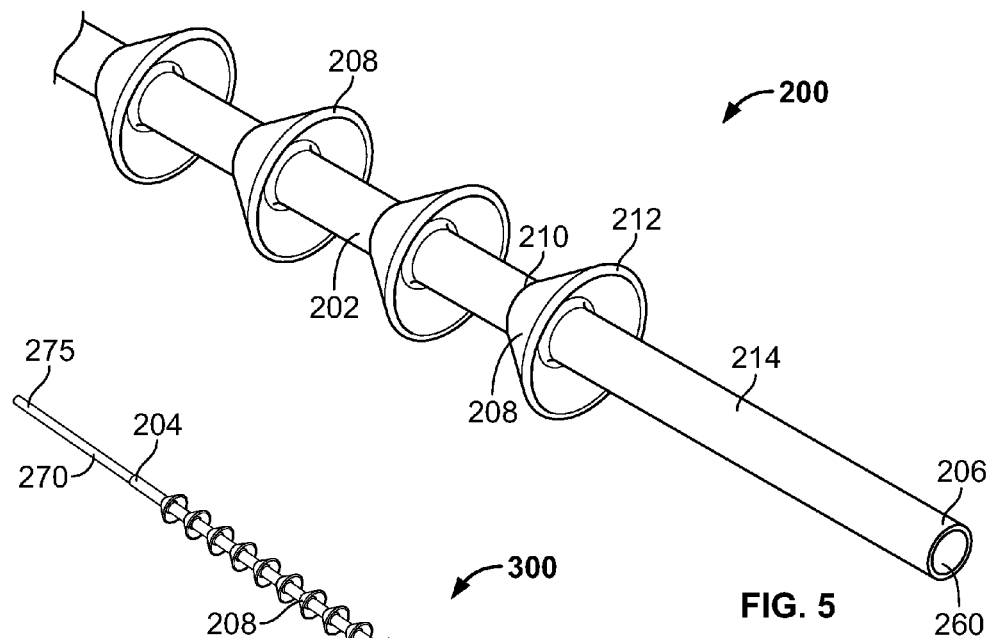
FIG. 5 shows a perspective view of a surgical suture having flexible protrusions, in accordance with one embodiment of the present invention.

Referring to FIG. 5, in one embodiment, a surgical suture 200 includes an elongated shaft 202 having a plurality of flexible protrusions 208 projecting therefrom. In the particular embodiment shown in FIG. 5, each of the flexible protrusions 208 has a conical shape including a base 210 adjacent an outer surface 214 of the shaft 202 and a flared edge 212 that is spaced from the outer surface 214 of the shaft 202. In one embodiment, the flared edge section 212 of each protrusion 208 preferably has a larger diameter than the base section 210 of the protrusion.

In one embodiment, the elongated shaft 202 preferably has a lumen 260 formed therein that extends between the ends of the shaft. In one embodiment, the lumen 260 defines an opening at one of the ends 206 of the elongated shaft 202. The lumen 260 may be adapted to receive a filament or monofilament. In the embodiment shown in FIG. 5, the lumen 260 extends between the trailing end 206 and the leading end (not shown) of the shaft 202. In at least one embodiment, the lumen 260 may extend only part way toward the opposite end of the shaft 202. In one embodiment, the lumen is a blind opening that only extends part way toward the opposite end of the shaft.

In one embodiment, a flowable material such as a pharmacological agent may be introduced into the lumen 260. The flowable material may migrate between the trailing end and the leading end of the shaft 202. In one embodiment, the flowable material may be pre-filled inside the hollow shaft 202 before implanting the surgical suture in tissue. In one embodiment, an injection tool such as a syringe having a needle may be used for introducing the flowable material into the lumen 260. The flowable material may also be introduced after the surgical suture is implanted in tissue. In one embodiment, the flowable material may be re-introduced into the lumen 260 after implantation. For example, a first dose of pharmacological agent may be introduced when the surgical suture is initially implanted in tissue. After a period of time, one or more additional doses of a pharmacological agent may be introduced into the lumen 260.

Figure 6A:
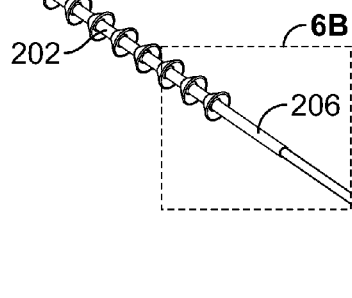
FIG. 6A shows a perspective view of a composite surgical suture including a tissue anchoring section and a filament, in accordance with one embodiment of the present invention.

Referring to FIG. 6A, in one embodiment, a composite surgical suture 300 includes a tissue anchoring element 200 including an elongated shaft 202 and a plurality of flexible protrusions 208 projecting from the elongated shaft 202. A first filament 270 may be secured to the leading end 204 of the tissue anchoring element 200 and a second filament 272 may be secured to the trailing end 206 of the tissue anchoring element 200.

Figure 6B:
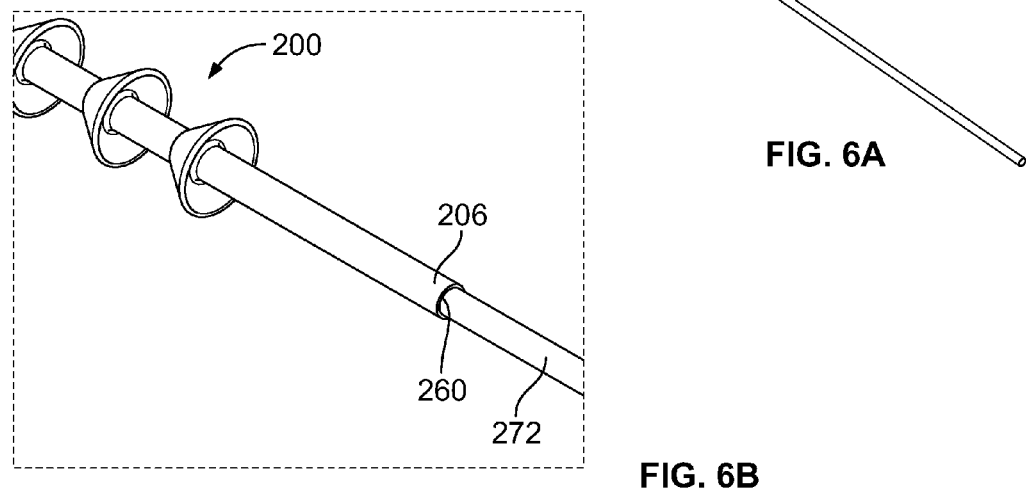
FIG. 6B shows an expanded view of a section of the composite surgical suture shown in FIG. 6A.

Referring to FIG. 6B, in one embodiment, the trailing end 206 of the tissue anchoring element 200 includes a lumen 260 formed therein. The filament 272 is preferably inserted into the lumen for being secured to the trailing end 206 of the tissue anchoring element 200. In one embodiment, the trailing end of the tissue anchoring element may not have a lumen and the filament may be secured directly to the trailing end of the tissue anchoring element.

Referring to FIG. 6A, in one embodiment, a tissue-piercing element such as a needle (not shown) may be secured to the leading end 275 of the filament 270 for advancing the composite surgical suture 300 through tissue or a prosthetic device. In one embodiment, the filament may include a plurality of filaments 270, 272. In some embodiments, the filaments may be monofilaments or multifilaments.

Figure 7:
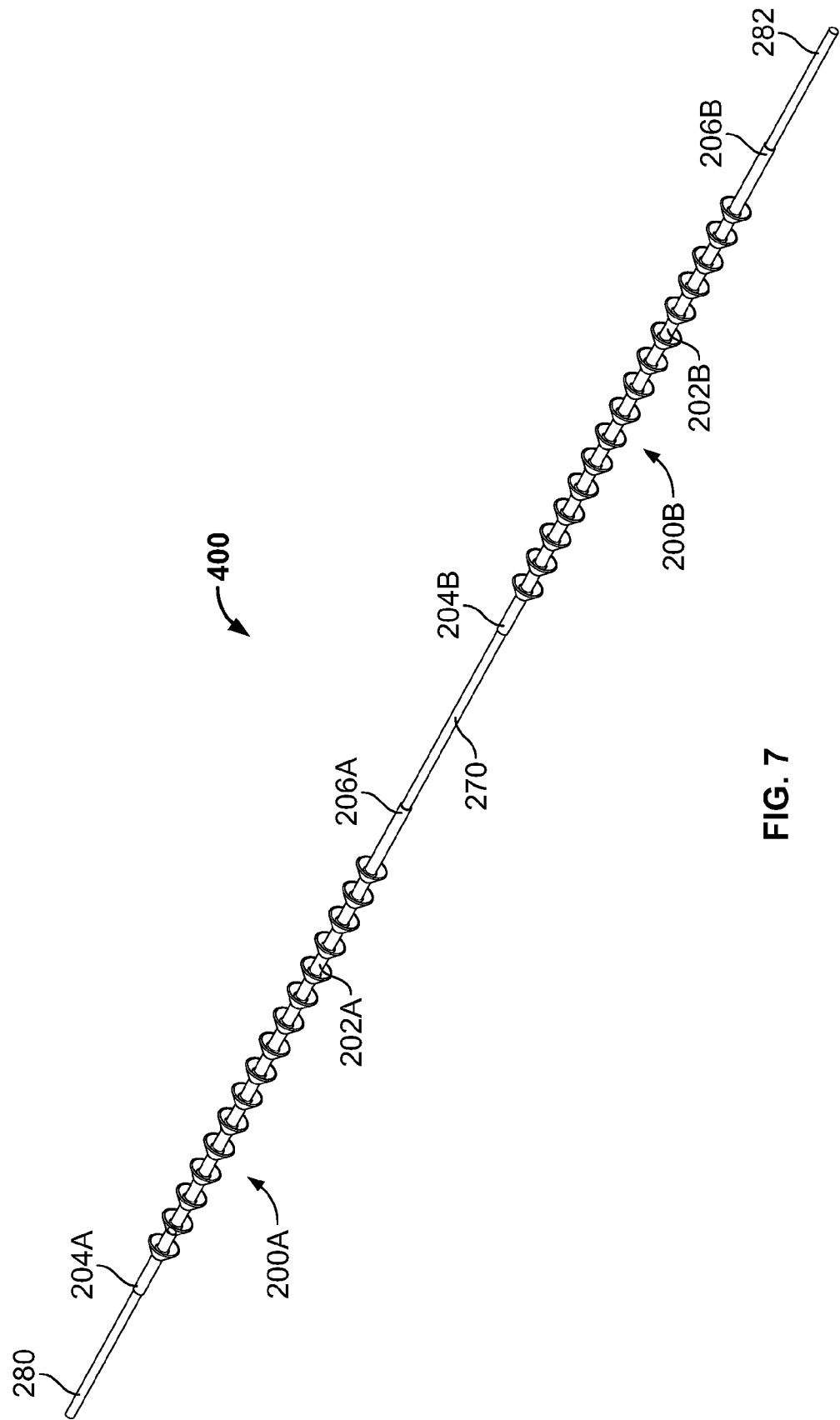
FIG. 7 shows a perspective view of a composite surgical suture, in accordance with one embodiment of the present invention.

Referring to FIG. 7, in one embodiment, a composite surgical suture 400 includes a first tissue anchoring element 200A and a tissue second anchoring element 200B coupled together by a filament 270 that extends between a trailing end 206A of the first tissue anchoring element 200A and a leading end 204B of the second tissue anchoring element 200B. In one embodiment, the elongated shafts 202A, 202B of the respective tissue anchoring elements 200A, 200B are hollow and the filament 270 passes completely through the hollow shafts of the two anchoring elements. In one embodiment, the opposing ends of the elongated shafts 202A, 202B have blind openings or lumens formed therein and smaller segments of filament 270 interconnect the two anchoring elements. In one particular embodiment, a first segment 270 of filament interconnects the trailing end 206A of the first anchoring element 200A with the leading end 204B of the second anchoring element 200B. A second segment 280 of filament is secured in an opening at a leading end 204A of the first anchoring element 200A, and a third segment 282 of filament is secured to an opening at the trailing end 206B of the second anchoring element 200B.

The composite surgical suture 400 shown in FIG. 7 preferably provides a multi-part device having one or more sections including flexible protrusions and one or more sections comprising a filament or mutlifilaments. The one or more filament sections of the suture may have the same, greater, or less flexibility than the tissue anchoring element sections of the suture. In one embodiment, the filament portions 270 may be absorbable and the tissue anchoring elements may be non-absorbable. In another embodiment, the filament sections may be non-absorbable and the anchoring element sections may be absorbable. In one embodiment, the entire composite surgical suture shown in FIG. 7 may be absorbable or non-absorbable.

Referring to FIG. 8, in one embodiment, a surgical suture 500 includes an elongated shaft 502 having a plurality of flexible protrusions 508 extending therefrom. Each of the flexible protrusions 508 is preferably collapsible inwardly toward the shaft 502. Each flexible protrusion 508 desirably includes a base 510 adjacent an outer surface 514 of the shaft 502 and a flared edge 512 spaced from the outer surface of the shaft. The flared edge 512 of each protrusion 508 preferably has a larger diameter than the base 510. At least one of the flexible protrusions 508 desirably includes an elongated slit 515 formed therein. The slit preferably provides a section on the flexible protrusion that more easily collapses inwardly toward the shaft 502. In the particular embodiment shown in FIG. 8, each of the flexible protrusions 508 includes at least one elongated slit 515. In one embodiment, the elongated slits 515 define straight lines. In one embodiment, a plurality of elongated slits 515 may be formed around the perimeter of each of the flexible protrusions 508. The elongated slits may be positioned at the same locations on each of the flexible protrusions so that each of the flexible protrusions collapse in a uniform configuration.

Referring to FIG. 9, in one embodiment, a surgical suture 600 includes an elongated shaft 602 having a plurality of flexible protrusions 608 projecting therefrom. Each of the flexible protrusions 608 includes a base 610 adjacent an outer surface of the shaft 608 and a flared edge 612 spaced from the outer surface of the shaft 602. In one embodiment, at least one of the flexible protrusions 608 includes a curved slit 615 formed therein. The curved slit 615 enables the flexible protrusion 608 to more easily collapse inwardly toward the shaft 602. In one embodiment, each of the flexible protrusions 608 includes at least one of the curved slits 615. In one embodiment, a plurality of curved slits 615 may be formed in each of the flexible protrusions 608. The curved slits 615 may be evenly spaced around the perimeter of the flexible protrusions 608.

Referring to FIG. 10A, in one embodiment, a surgical suture 700 includes an elongated shaft 702 having a leading end 704 and a trailing end 706. The surgical suture 700 includes a plurality of flexible protrusions 708 projecting outwardly from the shaft 702. Referring to FIG. 10B, in one embodiment, each of the flexible protrusions 708 is divided into a plurality of spaced flexible elements 725A-725D having spaces 735A-735D extending between each of the adjacent flexible elements 725A-725D. The spaces 735A-735D between the adjacent flexible elements desirably increase the flexibility of the flexible protrusions 708 and reduce the mass passing through the tissue and/or prosthetic devices. In one embodiment, each of the flexible protrusions 708 includes a plurality of the spaced flexible elements that are spaced from one another around the outer surface of the shaft 702. In one embodiment, the spaced flexible elements 725A-725D are preferably evenly spaced from one another. In FIG. 10B, four equally spaced flexible sections 725A-725D are shown. In other embodiments, however, a greater number of flexible sections (e.g. six, eight, etc.) may be provided.

Referring to FIG. 11, in one embodiment, a surgical suture includes a plurality of flexible protrusions 808 provided along the length of an elongated shaft 802. Each of the flexible protrusions 808 includes two or more evenly spaced flexible elements 825A-825D that extend around the perimeter of the shaft 802. In the particular embodiment shown in FIG. 11, four flexible elements 825A-825D are evenly spaced around the outer surface of the shaft 802. In one embodiment, web sections 835A-835D extend between the adjacent flexible elements 825A-825D. The web sections 835A-835D interconnect the flexible elements 825A-825D, thereby providing flexibility for the flexible elements while coupling the flexible elements together to provide more holding force. In one embodiment, the web sections 835A-835D may include filaments extending between the adjacent flexible elements 825A-835D. In one embodiment, the web sections may include mesh or biocompatible mesh extending between the adjacent flexible elements 825A-825D.

Figure 12:
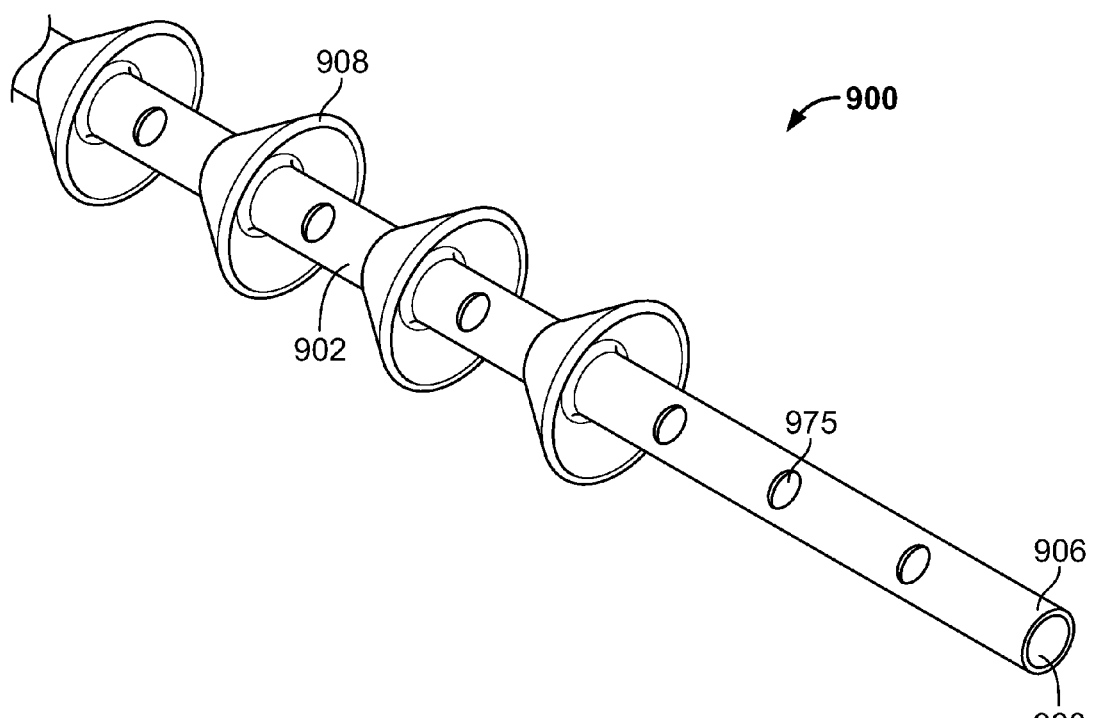
FIG. 12 shows a perspective view of a surgical suture having a shaft with a lumen extending along the length of the shaft, in accordance with one embodiment of the present invention.

Referring to FIG. 12, in one embodiment, a surgical suture 900 includes an elongated shaft 902 having a plurality of flexible tissue anchoring protrusions 908 projecting therefrom. The elongated shaft 902 has a leading end (not shown) and a trailing end 906. The surgical suture 900 includes a lumen 960 that extends between the trailing end 906 and the leading end (not shown) of the elongated shaft 902. The elongated shaft 902 has an outer surface with a plurality of openings 975 formed therein. The plurality of openings 975 are preferably in communication with the lumen 960 extending along the length of the shaft 902. A flowable material such as a pharmacological agent may be introduced into the lumen 960. When the surgical suture 900 is implanted in tissue or in a prosthetic device, the flowable material preferably flows from the lumen and through the plurality of opening 975 extending along the length of the shaft 902. The plurality of openings 975 extending through the outer wall of the shaft 902 allows delivery of the flowable material to the tissue and/or the prosthetic device surrounding the suture. The flowable material may be pre-filled inside the elongated opening 960 as the surgical suture is initially implanted in the tissue and/or the prosthetic device. The flowable material may also be introduced into the elongated opening after the surgical suture has been implanted. In one embodiment, additional doses of the flowable material may be introduced into the lumen 960 for delivery through the plurality of openings 975 extending along the length of the elongated shaft 902. The additional doses of the flowable material may be introduced after implantation of the surgical suture in tissue.

While the foregoing is directed to embodiments of the present invention, other and further embodiments of the invention may be devised without departing from the basic scope thereof. As such, the scope of the present invention is to be limited only as set forth in the appended claims.

What is claimed is:

1. A surgical suture comprising:
   a shaft having a leading end, a trailing end, and a lumen extending between the leading and trailing ends; and
   a plurality of flexible protrusions extending from said shaft and ending in rings with circular edges;
   wherein at least one of said flexible protrusions is divided into two or more flexible elements spaced from one another along said circular edge and around said shaft.

2. The surgical suture as claimed in claim 1, further comprising at least one filament extending through said lumen.

3. The surgical suture as claimed in claim 2, wherein said filament is secured to said shaft.

4. The surgical suture as claimed in claim 2, wherein sad shaft or said at least one filament is absorbable.

5. The surgical suture as claimed in claim 2, wherein said at least one filament is more flexible than said shaft.

6. The surgical suture as claimed in claim 1, wherein said lumen is located inside said shaft and is adapted to receive a flowable material.

7. The surgical suture as claimed in claim 6, wherein said shaft has an outer surface extending between the leading and trailing ends thereof, and a plurality of openings extending through the outer surface that are in communication with said lumen.

8. The surgical suture as claimed in claim 7, wherein said shaft includes a first axial opening at the leading end thereof in communication with said lumen and a second axial opening at the trailing end thereof in communication with said lumen.

9. The surgical suture as claimed in claim 7, further comprising a flowable material disposed in said lumen, wherein said flowable material is adapted to pass from said lumen and through said plurality of openings in the outer surface of said shaft.

10. The surgical suture as claimed in claim 9, wherein said flowable material is selected from the group of flowable material consisting of pharmacological agents, adhesives, epoxies, and polymers.

11. The surgical suture as claimed in claim 1, wherein said flexible elements have opposing edges and at least one web extends between at least two of the opposing edges.

12. The surgical suture as claimed in claim 11, wherein said at least one web is selected from a group of materials consisting of mesh, fabric, tethers, thread, and filaments.

13. A surgical suture comprising:
a shaft having a leading end, a trailing end, and a lumen extending between the leading and trailing ends thereof;
a plurality of flexible protrusions extending in a common direction from the outer surface of said shaft and ending in flared rings, wherein at least one of said flexible protrusions is divided into two or more flexible elements spaced from one another around the outer surface of said shaft, wherein said flexible elements have opposing edges; and
at least one web extending between at least two of the opposing edges of said flexible elements.

14. The surgical suture as claimed in claim 13, wherein said at least one web is selected from a group of materials consisting of mesh, fabric, tethers, thread, and filaments.

15. The surgical suture as claimed in claim 13, wherein said shaft includes a plurality of openings extending through the outer surface thereof that are in communication with said lumen.

16. The surgical suture as claimed in claim 13, further comprising a first axial opening provided at the leading end of said shaft and a second axial opening provided at the trailing end of said shaft, wherein said first and second axial openings are in communication with said lumen.

17. The surgical suture as claimed in claim 16, further comprising a flowable material introducible through one of said first and second axial openings and into said lumen, wherein said flowable material is adapted to pass through said plurality of openings in the outer surface of said shaft.

18. The surgical suture as claimed in claim 13, further comprising a filament extending through said lumen.

19. The surgical suture as claimed in claim 18, wherein said filament is secured to said shaft.

20. The surgical suture as claimed in claim 18, wherein said filament and said shaft have different levels of flexibility.

21. A surgical suture comprising:
a shaft having a leading end, a trailing end, and an outer surface extending between the leading and trailing ends thereof; and
a plurality of flexible protrustion extending from the outer surface of said shaft and ending in flared rings with circular edges, at least one of said flared rings comprising flexible elements that are spaced from one another and extending around the outer surface of said shaft.

* * * * *